United States Patent [19]

Kunz et al.

[11] 4,296,118
[45] Oct. 20, 1981

[54] FUNGICIDAL 3-[N-(PYRAZOL-1-YL-ACETYL)-N-(SUBSTITUTED PHENYL)]-AMINO-TETRAHYDRO-2-FURANONES

[75] Inventors: Walter Kunz, Oberwil, Switzerland; Wolfgang Eckhardt, Lörrach, Fed. Rep. of Germany; Adolf Hubele, Magden, Switzerland

[73] Assignee: Ciba-Geigy Corporation, Ardsley, N.Y.

[21] Appl. No.: 180,266

[22] Filed: Aug. 22, 1980

Related U.S. Application Data

[62] Division of Ser. No. 2,490, Jan. 11, 1979, abandoned, which is a division of Ser. No. 873,585, Jan. 30, 1978, Pat. No. 4,147,792.

[30] Foreign Application Priority Data

Feb. 4, 1977 [CH] Switzerland .......................... 1381/77
Mar. 28, 1977 [CH] Switzerland .......................... 3884/77

[51] Int. Cl.$^3$ ..................... A01N 43/56; A01N 43/08; C07D 405/12
[52] U.S. Cl. ................................ 424/273 P; 548/374
[58] Field of Search ..................... 548/374; 424/273 P

[56] References Cited

U.S. PATENT DOCUMENTS

| | | | |
|---|---|---|---|
| 3,933,860 | 1/1976 | Chan | 424/274 |
| 4,055,410 | 10/1977 | Cheng | 548/183 |
| 4,153,712 | 5/1979 | Hubele | 548/378 |
| 4,233,308 | 11/1980 | Kunz | 548/374 |

FOREIGN PATENT DOCUMENTS 2804299 8/1978 Fed. Rep. of Germany .

OTHER PUBLICATIONS

Ciba-Geigy, Chem. Abst., 1979, vol. 91, No. 103,714u.

*Primary Examiner*—Henry R. Jiles
*Assistant Examiner*—Natalie Harkaway
*Attorney, Agent, or Firm*—Frederick H. Rabin

[57] ABSTRACT

N-Acylated N-phenyl-aminotetrahydro-2-furanones of the formula are valuable fungicidal active substances. They can be used as fungicidal compositions, particularly for combating phytopathogenie fungi, e.g. against downy mildew on potatoes, tomatoes, grape vines and sugar beet and other plants. The novel compounds having a systemic action.

4 Claims, No Drawings

FUNGICIDAL 3-[N-(PYRAZOL-1-YL-ACETYL)-N-(SUBSTITUTED PHENYL)]-AMINO-TETRAHYDRO-2-FURANONES

This is a divisional of application Ser. No. 2, 490 filed on Jan. 11, 1979, now abandoned, which is a division of application Ser. No. 873,585 filed on Jan. 30, 1978 now U.S. Pat. No. 4,147,792.

The present invention relates to compounds of the formula I

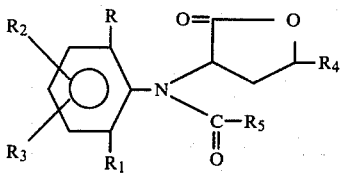

wherein
R represents $C_1$–$C_4$-alkyl, $C_1$–$C_4$-alkoxy or halogen,
$R_1$ represents $C_1$–$C_3$-alkyl, $C_1$–$C_4$-alkoxy or halogen,
$R_2$ represents hydrogen, $C_1$–$C_3$-alkyl, $C_1$–$C_4$-alkoxy or halogen,
$R_3$ represents hydrogen or methyl, with the total number of C atoms of the substituents R, $R_1$, $R_2$ and $R_3$ in the phenyl ring not exceeding the number 8,
$R_4$ represents hydrogen or methyl, whilst
$R_5$ represents one of the following groups:
an alkylthioalkyl or alkoxyalkyl group having 2 to 5 carbon atoms or an alkoxyalkoxymethyl group having a maximum of 6 carbon atoms, a 2-furanyl or 2-tetrahydrofuranyl group optionally substituted by halogen, a 1,2,4-triazolylmethyl group, a 1,2-pyrazolylmethyl group, or a group —$CH_2$—$OR_6$ in which $R_6$ represents a 5- or 6-membered heterocycle having oxygen as the hetero atom; to processes for producing these compounds; to compositions containing these compounds as active substances; and to the use of these active substances as microbicides in the protection of plants.

By alkyl or as alkyl moiety of an alkylthio or alkoxy group are meant, depending on the given number of carbon atoms, the following groups: methyl, ethyl, propyl, isopropyl, butyl, isobutyl, sec.-butyl or tert.-butyl. Alkoxyalkoxy groups are, in particular, methoxymethoxy, ethoxymethoxy, 1-methoxyethoxy and 1-ethoxyethoxy.

By halogen is meant fluorine, chlorine, bromine or iodine. $R_6$ represents preferably a tetrahydrofuranyl or pyranyl group, particularly one bound in the 2-position.

In the U.S. Pat. No. 3,933,860 are described 3-(N-acyl-N-arylamino)-lactones and -lactams as fungicides which are derived from the structure of benzoyl-, alkanoyl- or haloalkanoyl-(particularly haloacetyl-)anilides. Anilides of this type are described in the literature in great numbers as herbicides, e.g. U.S. Pat. Nos. 3,403,994, 3,442,945, 3,547,620, 3,637,847, 3,598,859 or 3,946,045.

It is therefore not surprising that the compounds given in U.S. Pat. No. 3,933,860 give rise in part, when applied in the amounts required in practice, to undesirable phytotoxicity in the plants to be protected from fungus infestation.

It has now been found that, surprisingly, compounds having the structure of the formula I have for practical requirements a very favourable microbicidal spectrum for the protection of cultivated plants, without affecting them disadvantageously by causing undesirable secondary effects. Within the scope of the present invention, cultivated plants are, for example, grain, maize, rice, vegetables, sugar beet, soya beans, peanuts, fruit trees and ornamental plants, especially however grape vines, hops, cucurbitaceae (cucumbers, pumpkins and melons), and solanaceae such as potatoes, tobacco and tomatoes, as well as bananas, cocoa plants and natural rubber plants.

Fungi occurring on plants or on parts of plants (fruit, blossom, foliage, stalks, tubers or roots) in these cultivated crops, or in related crops, can be inhibited or destroyed by application of the active substances of the formula I; and also parts of plants subsequently growing remain protected from such fungi. The active substances are effective against the phytopathogenic fungi belonging to the following classes: Ascomycetes (e.g. Erysiphaceae); Basidiomycetes, such as in particular rust fungi; Fungi imperfecti (e.g. Moniliales); but especially against Oomycetes belonging to the Phycomycetes class, such as Phytophthora, Peronospora, Pseudoperonospora, Pythium or Plasmopara. Furthermore, the compounds of the formula I have a systemic action. They can be used also as dressing agents for treating seeds (fruits, tubers and grain) and plant cuttings to preserve them from fungus infections; and they can be used also against phytopathogenic fungi occurring in the soil.

Preferred compounds of the formula I as plant fungicides are those wherein R represents methyl, $R_1$ represents methyl, ethyl, chlorine or bromine, $R_2$ represents hydrogen, halogen or methyl, and $R_3$ represents hydrogen or methyl, while $R_4$ and $R_5$ have the meanings given for the formula I. These are to be referred to as compound group Ia.

An important subgroup of the compound group Ia is formed by those compounds wherein $R_5$ represents an alkylthioalkyl or alkoxyalkyl group having 2 to 5 carbon atoms, a 2-furanyl or 2-tetrahydrofuranyl group optionally substituted by halogen, or a 1,2,4-triazolylmethyl group. This subgroup is to be called compound group Ib.

Compounds to be emphasised among these compounds of the group Ib by virtue of their effectiveness are those wherein $R_5$ represents methoxymethyl or ethoxymethyl. These are to be called compound group Ic.

Particularly preferred active substances within the compound group Ia, on account of their advantageous action, are those wherein $R_5$ represents the 1,2,4-triazol-1-ylmethyl group. These are to be designated as compound group Id.

A further important subgroup of the compound group Ia is formed by those compounds wherein $R_5$ represents a 2-furanyl or 2-tetrahydrofuranyl group optionally substituted by halogen. This subgroup is to be termed compound group Ie.

Another important subgroup of the compound group Ia is made up of those compounds wherein $R_5$ represents a 1,2-pyrazolylmethyl group. This subgroup is to be referred to as a compound group If.

Yet another important subgroup of the compound group Ia is composed of those compounds wherein $R_5$ represents an alkoxyalkoxymethyl group having a maximum of 5 carbon atoms. This subgroup is to be identified as compound group Ig.

The compounds of the formula I are produced according to the invention (A) by acylation of a compound of the formula II

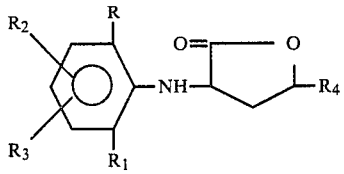

with a compound of the formula III

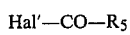

or to obtain derivatives with $R_5$=1,2,4-triazolylmethyl, 1,2-pyrazolylmethyl or alkylthio (B) by initial monohaloacetylation of a compound of the formula II to give a compound of the formula IV

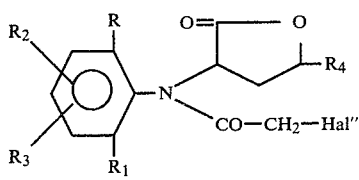

and further reaction selectively with 1,2,4-triazole, 1,2-pyrazole or alkylmerkaptan, or with the metal salt of one of these reactants, preferably with the alkali metal salt or alkaline-earth metal salt; or to obtain derivatives with $R_5$=alkoxyalkoxymethyl or —$CH_2$—$OR_6$ (C) by initial monohaloacetylation of a compound of the formula II to give a compound of the formula IV, exchange of the reactive substituent Hal" for a lower alkanecarboxylic acid, or for one of the alkali metal salts or alkaline-earth metal salts thereof, to obtain an acyloxyacetylanilide of the formula V

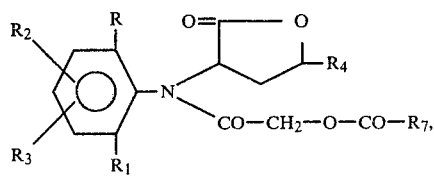

from which there is then obtained by mild alcoholysis with e.g. an alkali alcoholate of a lower alcohol, such as methanol or ethanol, and acidification the corresponding hydroxyacetanilide, which is activated with alkali metal, alkali hydride or p-toluenesulphonic acid, and reacted selectively with alkoxyalkyl halide or 2,3-dihydrofuran or 3,4-dihydro-2H-pyrane; or (D) by reaction of an already acylated aniline of the formula VI

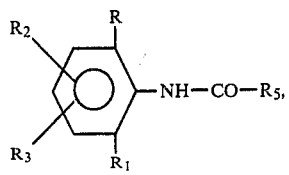

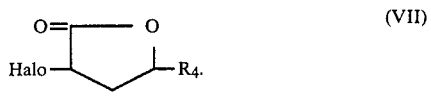

in the presence of a proton acceptor such as butyllithium or sodium hydride, with a 2-halo-4-butyrolactone of the formula VII

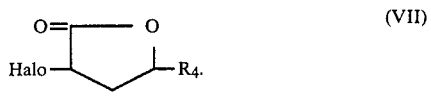

In the formula II, III, IV, V, VI and VII, the symbols R to $R_5$ have the meanings given under the formula I, and Halo, Hal' and Hal" represent halogen, preferably chlorine or bromine. $R_7$ is a lower alkyl group having less than 7 C atoms.

The reactions can be performed in the presence or absence of solvents or diluents which are inert to the reactants. The following are for example suitable: aliphatic or aromatic hydrocarbons such as benzene, toluene, xylenes or petroleum ether; halogenated hydrocarbons such as chlorobenzene, methylene chloride, ethylene chloride or chloroform; ethers and ethereal compounds such as dialkyl ether, dioxane or tetrahydrofuran; nitriles such as acetonitrile; N,N-dialkylated amides such as dimethylformamide; dimethylsulphoxide, ketones such as methyl ethyl ketone, and mixtures of such solvents with each other.

For acylation according to process A or C, or for monohaloacetylation according to process B, it is possible to use the corresponding carboxylic acids themselves and also the esters thereof, advantageously however the acid anhydrides or, as given in the case of formula III, the acid halides, preferably the acid chlorides or acid bromides.

The reaction temperatures are between 0° and 180° C., preferably between 20° and 120°. The use of acid-binding agents or condensation agents is advantageous in some cases. Suitable as such are tertiary amines such as trialkylamines (e.g. triethylamine), pyridine and pyridine bases, or inorganic bases, such as the oxides and hydroxides, hydrogen carbonates and carbonates of alkali metals and alkaline-earth metals, and also sodium acetate.

The production process A starting with compounds of the formula II, and likewise the acylation stage leading to compounds of the formula IV, can be performed also without acid-binding agents; in some cases, however, the passing through of nitrogen to expel the formed hydrogen halide is advisable. In other cases, an addition of dimethylformamide as a reaction catalyst is very advantageous.

Details regarding the production of the intermediates of the formula II are known.

The compounds of the formula I possess in the lactone radical

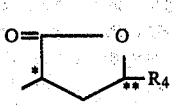

a (\*) center of asymmetry and, where $R_4=CH_3$, a second (\*\*) center of asymmetry, and can be resolved in the customary manner (e.g. fractional crystallisation or chromatographical separation) into optical antipodes. In this respect, the different configurations have a varyingly strong microbicidal action. Centers of asymmetry can occur also in the case of some substituents $R_5$. Provided that no specific synthesis for the isolation of the pure isomers of the formula I or of the employed butyrolactone is performed, a product is usually obtained as an isomeric mixture.

The following Examples serve to further illustrate the invention without however limiting the scope thereof. The temperatures are in degrees Centigrade.

The following compounds belong to a class of particularly effective plant fungicides:

3-[N-(methoxyacetyl)-N-(2,6-dimethylphenyl)]-aminotetrahydro-2-furanone,

3-[N-(ethoxyacetyl)-N-(2,6-dimethylphenyl)]-aminotetrahydro-2-furanone,

3-[N-(methoxyacetyl)-N-(2,6-dimethyl-3-chlorophenyl)]-aminotetrahydro-2-furanone, 3-[N-(ethoxyacetyl)-N-(2,6-dimethyl-3-chlorophenyl)]-aminotetrahydro-2-furanone, 3-[N-(methoxyacetyl)-N-(2,6-dimethylphenyl)-]amino-5-methyltetrahydro-2-furanone, 2,6-dimethyl-N-(3-tetrahydrofuran-2-one)-2-tetrahydrofuroylanilide, 2,3,6-trimethyl-N-(3-tetrahydrofuran-2-one)-2-tetrahydrofuroylanilide, 2,6-dimethyl-4-chloro-N-(3-tetrahydrofuran-2-one)-2-tetrahydrofuroyl-anilide, 3-[N-(methoxyacetyl)-N-(2,3 5,6-tetramethylphenyl)]-aminotetrahydro-2-furanone, and 2,3,5,6-tetramethyl-N-(3-tetrahydrofuran-2-one)-2-furoylanilide.

EXAMPLE 1

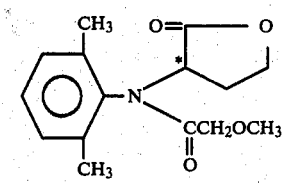

Production of

3-[N-(methoxyacetyl)-N-(2,6-dimethylphenyl)]-aminotetrahydro-2-furanone (compound No. 2)

(a) 165 g of 2-bromo-4-butyrolactone is slowly added to 121 g of 2,6-dimethylaniline and 106 g of sodium carbonate in 750 ml of dimethylformamide, and then stirred for 30 hours at 100°. After cooling, the unreacted aniline and the solvent are distilled off in vacuo; the residue is added to water and extracted three times with methylene chloride. The extracts are washed with water, dried over sodium sulphate, and then freed from solvent. After recrystallisation from petroleum ether/diethyl ether (1:10), the residue melts at 79°–83°.

(b) 11.9 g of methoxyacetyl chloride in 20 ml of toluene is added, with stirring, to 20.5 g of the intermediate product, obtained according to (a), in 80 ml of abs. toluene, whereupon the temperature rises from 25° to 35°. The reaction mixture is refluxed for six hours and, after the addition of active charcoal, filtered through Hyflo; it is then concentrated by evaporation and recrystallised from ethyl acetate/petroleum ether, m.p. 124°–127°.

EXAMPLE 2

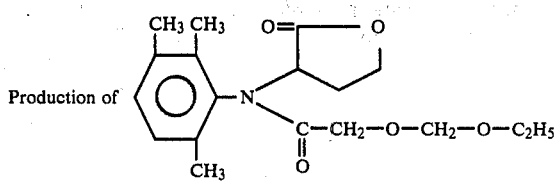

Production of

N-(3'-tetrahydrofuranone-2')-N-ethoxymethoxyacetyl-2,3,6-trimethylaniline (compound No. 14)

(a) 0.5 g of sodium is dissolved in 10 ml of absolute methanol. There is then added dropwise, with stirring, a solution of 21.4 g of 3-[N-acetoxyacetyl)-N-(2,3,6-trimethylphenyl)]-aminotetrahydro-2-furanone in 60 ml of abs. methanol at 20°–25°. Stirring is continued overnight at room temperature; the reaction mixture is subsequently concentrated in a rotary evaporator, and 500 ml of ice water is added. The suspension is then adjusted with 1% hydrochloric acid, with ice cooling, to pH 2 (acidified to Congo red); it is filtered with suction and then washed with water until neutral. The 3-[N-(hydroxyacetyl)-N-(2,3,6-trimethylphenyl)]-aminotetrahydrofuranone-2, occurring as a mixture of diastereoisomers, has a melting point of 151°–155° after being recrystallised from isopropanol.

(b) In a nitrogen atmosphere, 1.3 g of sodium hydride (as a 55% oil dispersion) is suspended in 50 ml of abs. tetrahydrofuran. There is then added dropwise at 0°–10° 13.8 g of the intermediate product obtained under (a), dissolved in 50 ml of abs. tetrahydrofuran. After completion of the generation of hydrogen (3 hours), a solution of 4.7 g of chloromethylethyl ether in 10 ml of tetrahydrofuran is added dropwise at 0°, and stirring is maintained for 20 hours at room temperature. Water is then carefully added, and extraction with ether is performed four times. The extracts are washed with water and dried over sodium sulphate. Concentration by evaporation yields a resin which, for the removal of paraffin oil, is digested four times with a small amount of petroleum ether; the elementary analysis of the resin obtained gives the following values:

found: C 64.1%, H 7.7%, N 4.0%, calculated: C 64.4%, H 7.5%, N 4.2%.

EXAMPLE 3

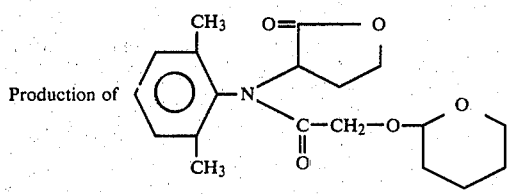

Production of

N-(3″-tetrahydrofuranone-2″)-N-2′-pyranyloxyacetyl-2,6-dimethylaniline (compound No. 43)

13.2 g of the 3-[N-hydroxyacetyl-N-(2,6-dimethylphenyl)]-amino-tetrahydrofuranone-2 obtained in a manner analogous to that described in Example 2a is suspended in 50 ml of abs. ethyl acetate, and a trace of p-toluenesulphonic acid is added. There is then added dropwise at room temperature in the course of 10 minutes, with stirring, a solution of 5.9 g of 3,4-dihydro-2-H-pyrane in 10 ml of abs. ethyl acetate. The reaction mixture is then stirred for a further 1¼ hours at room temperature; it is subsequently cooled to 0° and 15 g of solid potassium carbonate is added. After stirring at 0° for 15 minutes, the mixture is filtered; thorough washing is then carried out with ethyl acetate, and the filtrate is concentrated by evaporation. On trituration with petroleum ether, the residue crystallises, and melts at 106°–112° (diastereoisomeric mixture).

There are produced in an analogous manner the following compounds of the formula ($R = CH_3$)
($R_1 = $ 6-position)

| Compound No. | $R_1$ | $R_2$ | $R_3$ | $R_4$ | $R_5$ | Physical constants |
|---|---|---|---|---|---|---|
| 1 | $CH_3$ | H | H | $CH_3$ | $—CH_2OCH_3$ | m.p. 109–110° |
| 2 | $CH_3$ | H | H | H | $—CH_2OCH_3$ | m.p. 124–127° |
| 5 | $C_2H_5$ | H | H | H | $—CH_2OCH_3$ | |
| 4 | $CH_3$ | H | H | $CH_3$ | $—CH_2OC_2H_5$ | |
| 5 | $CH_3$ | H | H | H | $—CH_2OC_2H_5$ | oil |
| 6 | Cl | H | H | H | $—CH_2OCH_3$ | |
| 7 | $CH_3$ | 3-$CH_3$ | H | H | $—CH_2OCH(CH_3)OC_2H_5$ | resin |
| 8 | $CH_3$ | H | H | H | $—CH_2OC_3H_7(n)$ | |
| 9 | $CH_3$ | 3-$CH_3$ | H | H | $—CH_2OCH_3$ | resin |
| 10 | Cl | H | H | H | $—CH_2OC_2H_5$ | |
| 11 | Br | 4-Cl | H | H | $—CH_2OCH_3$ | |
| 12 | $CH_3$ | 3-$CH_3$ | H | H | $—CH_2OC_2H_5$ | resin |
| 13 | $CH_3$ | 4-Cl | H | H | $—CH_2CH_2OCH_3$ | |
| 14 | $CH_3$ | 3-$CH_3$ | H | H | $—CH_2OCH_2OC_2H_5$ | resin |
| 15 | $CH_3$ | 3-$CH_3$ | H | $CH_3$ | $—CH_2OCH_3$ | |
| 16 | $CH_3$ | H | H | H | $—CH_2OC_3H_7(i)$ | |
| 17 | $CH_3$ | H | H | H | $—CH_2CH_2OCH_3$ | b.p. 178–185°/ 0,1 Torr |
| 18 | $CH_3$ | 3-$CH_3$ | 5-$CH_3$ | H | $—CH_2OC_3H_7(i)$ | |
| 19 | $CH_3$ | 3-$CH_3$ | 5-$CH_3$ | H | $—CH_2OCH_3$ | m.p. 111–114° |
| 20 | $CH_3$ | 4-Cl | H | H | $—CH_2OC_2H_5$ | m.p. 105–106° |
| 21 | $CH_3$ | 3-$CH_3$ | H | $CH_3$ | $—CH_2CH_2OCH_3$ | |
| 22 | $CH_3$ | H | H | H | $—CH_2OCH_2OCH_3$ | oil |
| 23 | $CH_3$ | 3-$CH_3$ | H | $CH_3$ | $—CH_2OC_2H_5$ | |
| 24 | $CH_3$ | 4-Cl | H | H | $—CH_2OCH_3$ | m.p. 111–113° |
| 25 | $CH_3$ | H | H | H | $—CH_2CH_2OC_2H_5$ | b.p. 160–165°/ 0,2 Torr |
| 26 | $CH_3$ | 3-$CH_3$ | 5-$CH_3$ | H | $—CH_2OC_2H_5$ | m.p. 81–83° |
| 27 | $CH_3$ | 3-$CH_3$ | H | H | $—CH_2—S—CH_3$ | m.p. 90–94° |
| 28 | $CH_3$ | H | H | H | $—CH_2—S—CH_3$ | m.p. 72–73° |
| 29 | $CH_3$ | 3-$CH_3$ | H | H | $—CH_2—O—$(tetrahydropyranyl) | m.p. 88–91° |
| 30 | $CH_3$ | 3-Cl | H | H | $—CH_2OCH_3$ | b.p. 190–200°/0,1 Torr |
| 31 | $CH_3$ | 4-Cl | H | $CH_3$ | $—CH_2OCH_3$ | |
| 32 | $CH_3$ | H | H | H | $—CH_2CH_2OC_3H_7(i)$ | |
| 33 | $CH_3$ | 3-Cl | H | H | $—CH_2OC_2H_5$ | b.p. 120–135°/0.06 Torr. |
| 34 | $CH_3$ | 3-$CH_3$ | 5-$CH_3$ | H | $—CH_2CH_2OCH_3$ | |
| 35 | $CH_3$ | 3-Cl | H | H | $—CH_2OC_3H_7(n)$ | |
| 36 | $CH_3$ | 4-Cl | H | $CH_3$ | $—CH_2OC_2H_5$ | |
| 37 | $CH_3$ | H | H | H | $—CH_2OCH_2CH_2OCH_3$ | b.p. 186–195°/ 0.1 Torr |
| 38 | $CH_3$ | 3-Cl | H | H | $—CH_2OC_3H_7(i)$ | |
| 39 | $CH_3$ | 3-$CH_3$ | H | H | $—CH_2OCH_2CH_2OCH_3$ | oil |
| 40 | $CH_3$ | 3-$CH_3$ | H | H | $—CH_2CH_2OC_2H_5$ | b.p. 190–193°/ 0,15 Torr |
| 41 | $CH_3$ | 3-Cl | H | H | $—CH_2CH_2OCH_3$ | |
| 42 | $CH_3$ | 3-Cl | H | H | $—CH_2CH_2OC_2H_5$ | |
| 43 | $CH_3$ | H | H | H | $—CH_2O—$(tetrahydropyranyl) | b.p. 106–112° |

-continued

| | | | | | | |
|---|---|---|---|---|---|---|
| 44 | CH₃ | H | H | H | —CH₂O—CH(CH₃)—OC₂H₅ | oil |
| 45 | CH₃ | 3-CH₃ | 5-CH₃ | H | —CH₂O—CH(CH₃)—OC₂H₅ | oil |
| 46 | CH₃ | 3-CH₃ | H | H | —CH₂CH₂OCH₃ | b.p. 182–185°/ 0,08 Torr |
| 47 | CH₃ | 3-CH₃ | 5-CH₃ | H | —CH₂O—⟨tetrahydropyran⟩ | m.p. 93–97° | and also the following derivatives with R = —OCH₃ and R₄ = H:

| Compound No. | R₁ | R₂ | R₃ | R₅ | Physical constants |
|---|---|---|---|---|---|
| 48 | CH₃ | H | H | —CH₂OCH₃ | m.p. 88–90° |
| 49 | Cl | H | H | —CH₂OCH₃ | |
| 50 | Br | 4-Cl | H | —CH₂OCH₃ | m.p. 79–83° |

EXAMPLE 4

Production of

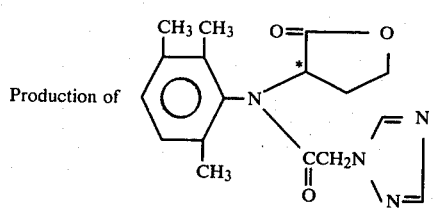

3-[N-(1,2,4-triazol-1-yl-acetyl)-N-(2,3,6-trimethylphenyl)]-amino-tetrahydro-2-furanone (compound No. 61)

(a) 165 g of 2-bromo-4-butyrolactone is slowly added at 10° to 135 g of 2,3,6-trimethylaniline and 106 g of sodium carbonate in 750 ml of dimethylformamide, and the mixture is subsequently stirred for 16 hours at 70° and for 24 hours at 100°. After cooling to +10°, there is added, with cooling, 1200 ml of ice water. Stirring is maintained at 10° for 2 hours; the precipitate is filtered off and subsequently washed with water and petroleum ether to leave 3-[N-(2,3,6-trimethylphenyl)]-amino-tetrahydro-2-furanone, m.p. 108°–110°.

(b) 11 g of the intermediate product obtained according to (a) is refluxed in 60 ml of abs. toluene with 6.2 g of chloroacetyl chloride for 4 hours; the solvent is distilled off after cooling, and the browish-coloured residue is recrystallised from ethyl acetate/petroleum ether (b.p. 40°–60°) to yield 3-[N-chloroacetyl-N-(2,3,6-trimethylphenyl)]-amino-tetrahydro-2-furanone, m.p. 92°–94°.

(c) 6.6 g of 1,2,4-triazole is added portionwise, in a nitrogen atmosphere, to 2.4 g of 50% sodium hydride dispersion in 100 ml of abs. dioxane, and refluxing is maintained until the generation of hydrogen has ceased. After cooling to +10°, there is added dropwise, with stirring, 8 g of the 3-[N-chloroacetyl-N-(2,3,6-trimethylphenyl)]-amino-tetrahydro-2-furanone in 100 ml of dioxane; the reaction mixture is refluxed for 16 hours in a nitrogen atmosphere and, after cooling, 100 ml of water is carefully added. The mixture is poured into ice water, and repeatedly extracted with methylene chloride. The combined extracts are washed with water, dried over sodium sulphate, filtered, and freed from solvent. After dissolving the residue in ethyl acetate, the solution is boiled with active charcoal and filtered hot, and petroleum ether (b.p. 40°–60°) is added to the still hot filtrate until it starts to become cloudy; the filtrate is then cooled and the final product is filtered off. On being heated, it commences to slowly decompose from 70°.

There are produced in an analogous manner the following compounds of the formula

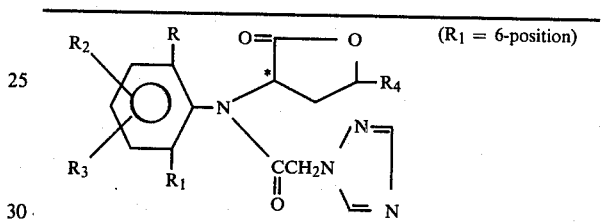

(R₁ = 6-position)

| Compound No. | R | R₁ | R₂ | R₃ | R₄ | Physical data |
|---|---|---|---|---|---|---|
| 51 | CH₃ | CH₃ | H | H | H | m.p. 133–135° |
| 52 | CH₃ | Cl | H | H | CH₃ | |
| 53 | CH₃ | C₂H₅ | H | H | H | |
| 54 | CH₃ | Cl | H | H | H | |
| 55 | CH₃ | CH₃ | 3-CH₃ | 5-CH₃ | H | oil |
| 56 | CH₃ | C₂H₅ | H | H | CH₃ | |
| 57 | CH₃ | CH₃ | H | H | CH₃ | |
| 58 | CH₃ | CH₃ | 3-CH₃ | 5-CH₃ | CH₃ | |
| 59 | CH₃ | CH₃ | 3-Cl | H | H | m.p. 48° (decomp.°) |
| 60 | CH₃ | CH₃ | 3-Br | H | CH₃ | |
| 61 | CH₃ | CH₃ | 3-CH₃ | H | H | decomposition from 70° |
| 62 | CH₃ | CH₃ | 3-Cl | H | CH₃ | |
| 63 | CH₃ | CH₃ | 3-Br | H | H | |
| 64 | CH₃ | CH₃ | 4-Cl | H | CH₃ | |
| 65 | CH₃ | CH₃ | 3-CH₃ | H | CH₃ | |
| 66 | CH₃ | CH₃ | 4-Cl | H | H | |
| 67 | CH₃ | Br | 4-Cl | H | H | |
| 68 | CH₃O | CH₃ | H | H | H | oil |
| 69 | CH₃O | Cl | H | H | H | |

There are produced in an analogous manner the following compounds of the formula

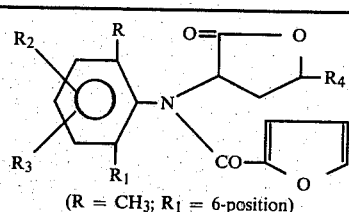

(R = CH₃; R₁ = 6-position)

| Compound No | R₁ | R₂ | R₃ | R₄ | Physical constants |
|---|---|---|---|---|---|
| 70 | CH₃ | H | H | H | m.p. 143–145° |
| 71 | CH₃ | 4-Cl | H | H | |
| 72 | CH₃ | H | H | CH₃ | m.p. 176–180° |
| 73 | C₂H₅ | H | H | H | |

-continued

| | | | | | |
|---|---|---|---|---|---|
| 74 | Cl | H | H | H | |
| 75 | Br | 4-Cl | H | H | |
| 76 | CH₃ | 3-Br | H | H | |
| 77 | CH₃ | 3-CH₃ | H | CH₃ | |
| 78 | CH₃ | 3-CH₃ | H | H | m.p. 132–133° |
| 79 | CH₃ | 3-Cl | H | H | m.p. 65° (decomp.) |
| 80 | CH₃ | 3-CH₃ | 5-CH₃ | H | m.p. 207–210° | and also the following derivatives with R = —OCH₃:

| Comp. No. | $R_1$ | $R_2$ | $R_3$ | $R_4$ | Physical constants |
|---|---|---|---|---|---|
| 81 | CH₃ | H | H | H | m.p. 164–165° |
| 82 | Cl | H | H | H | m.p. 152–153° |
| 83 | Cl | 4-Cl | H | H | |
| 84 | Br | 4-Br | H | H | |
| 85 | Br | H | H | H | |
| 86 | Cl | H | H | CH₃ | | and the compounds

No. 87 [structure: 2-CH₃, 6-Cl phenyl-N with tetrahydrofuranone and CO—furan—Br]

No. 88 [structure: 2-OCH₃, 6-Cl phenyl-N with tetrahydrofuranone and CO—furan—Br] m.p. 164–165°

No. 89 [structure: 2,6-di-CH₃ phenyl-N with tetrahydrofuranone and CO—furan—Br] m.p. 158–160°

There are produced in an analogous manner the following compounds of the formula

[structure with R, $R_1$, $R_2$, $R_3$, $R_4$ substituents on phenyl-N-tetrahydrofuranone-CO-tetrahydrofuran]

(R = CH₃; $R_1$ = 6-position)

| Comp. No. | $R_1$ | $R_2$ | $R_3$ | $R_4$ | Physical constants |
|---|---|---|---|---|---|
| 90 | CH₃ | H | H | H | m.p. 142–146° |
| 91 | CH₃ | H | H | CH₃ | |
| 92 | C₂H₅ | H | H | H | |
| 93 | Cl | H | H | H | |
| 94 | CH₃ | 4-Cl | H | H | m.p. 137–139° |
| 95 | CH₃ | 3-CH₃ | H | H | m.p. 112–113° |
| 96 | CH₃ | 4-Cl | H | CH₃ | |
| 97 | CH₃ | 3-CH₃ | 5-CH₃ | H | oil | as well as the following derivatives with R = —OCH₃:

| Compound No. | $R_1$ | $R_2$ | $R_3$ | $R_4$ | |
|---|---|---|---|---|---|
| 98 | CH₃ | H | H | H | oil |
| 99 | Cl | H | H | H | |
| 100 | Cl | 4-Cl | H | H | |
| 101 | Br | 4-Br | H | H | |
| 102 | Br | H | H | H | |
| 103 | Cl | H | H | CH₃ | |

EXAMPLE 5

Production of [structure of compound No. 111: 2,6-dimethyl phenyl-N-(tetrahydrofuranone)-COCH₂N-pyrazolyl]

3-[N-(1,2-pyrazol-1-yl-acetyl)-N-(2,3,6-trimethyl-phenyl)]-amino-tetrahydro-2-furanone (compound No. 111)

(a) Production of 2-(1-pyrazolyl)-acetic acid 50 g of pyrazole in 250 ml of abs. tetrahydrofuran is added dropwise in a nitrogen atmosphere within ½ hour at 20°–30°, with stirring and cooling, to 38.7 g of sodium hydride in 100 ml of abs. tetrahydrofuran. The reaction mixture is stirred for a further 3 hours at 40°; it is then cooled towards 5° and, with good cooling, 160.7 g of bromoacetic acid ethyl ester in 100 ml of abs. tetrahydrofuran is added dropwise at 0°–10° during 1 hour. Stirring is maintained overnight at room temperature; there is then added dropwise 150 ml of ethanol; stirring is continued for 1 hour, and the suspension is subsequently concentrated by evaporation. To the residue is added a solution of 74 g of NaOH tablets in 600 ml of 60% methanol (aqueous), and refluxing is carried out for 40 minutes. The solution is then cooled, and washed twice with 200 ml of ether. The aqueous phase is made acid to a congo-red indicator (about pH 2) with conc. hydrochloric acid at 5° with cooling, and the solution is continuously extracted during 24 hours with methylene chloride. The extract is concentrated by evaporation, and recrystallised from ether/tetrahydrofuran. The crystals melt at 167°–169°.

(b) 165 g of 2-bromo-4-butyrolactone is slowly added at 10° C. to 135 g of 2,3,6-trimethylaniline and 106 g of sodium carbonate in 750 ml of dimethylformamide, and the mixture is subsequently stirred for 16 hours at 70° and for 24 hours at 100°. After cooling to +10°, there is added, with cooling, 1200 ml of ice water. Stirring is continued at 10° for 2 hours; the precipitate is filtered off, and washed with water and petroleum ether to yield 3-[N-2,3,6-trimethylphenyl)]-amino-tetrahydro-2-furanone, m.p. 108°–110°.

(c) 6.3 g of 2-(1-pyrazolyl)-acetic acid is placed into 200 ml of toluene; 6.2 g of thionyl chloride is added, and the mixture is refluxed for 1 hour. It is then cooled to 20°, and 11 g of the intermediate obtained according to a) and 5.8 g of sodium carbonate are added. After stirring overnight at room temperature, ice water is added, and extraction is performed with methylene chloride; the extracts are washed with water, dried over sodium sulphate and concentrated by evaporation. The resin remaining is purified through a silica gel column, and finally frozen out from ether at −50°. The vitreous diastereoisomeric mixture of 3-[N-(1,2-pyrazol-1-yl-acetyl)-N-2,3,6-trimethylphenyl)]-amino-tetrahydrofuranone melts at 50°–60°.

There are produced in an analogous manner the following compounds of the formula suitable pesticides, such as fungicides, insecticides, acaricides, nematocides, rodenticides or herbicides, or with active substances affecting plant growth and also with fertilisers.

EXAMPLE 6

Action against Phytophthora infestans on tomatoes (I) Curative action

Tomato plants of the variety "Roter Gnom" are sprayed, after three weeks' cultivation, with a zoospore suspension of the fungus, and incubated in a chamber at 18° to 20° with saturated atmospheric humidity. The incubation treatment is interrupted after 24 hours; the plants are dried and then sprayed with a liquor containing the active substance in the form of a wettable powder at a concentration of 0.06% and 0.02%. The applied coating is allowed to dry, and the plants are subsequently returned to the moist-atmosphere chamber for 4 days. The number and size of the typical leaf spots appearing after this time serve as a criterion for an assessment of the effectiveness of the substances tested. Compounds of the formula I consistently produced, at an active-substance concentration of 0.06%, a reduction of fungus infestation to less than 20%. The compounds Nos. 1, 2, 5, 12, 19, 24, 28, 30, 33, 51, 61, 70, 79, 80, 82, 89, 90, 95, 98, 111 and others brought about at this concentration a reduction of fungus infestation to 0–5%. At the concentration of active substance of 0.02%, a reduction of fungus infestation to 0–5% was produced by, inter alia, the compounds Nos. 1, 2, 5, 12, 19, 28, 30, 33, 70, 79, 80, 90 and 95. No phytotoxicity was observed.

(II) Preventitive systemic action

The active substance in the form of a wettable powder is applied in a concentration of 0.006% (relative to the volume of soil) to the surface of the soil around 3-week old potted tomato plants of the "Roter Gnom" variety. After a period of three days, the under side of the leaves of the plants is sprayed with a zoospore suspension of Phytophthora infestans. The plants are then stored for 5 days in a spray chamber at 18°–20° with a saturated atmosphere. The typical leaf spots appear after this time; on the basis of their number and size, an evaluation is then made of the effectiveness of the substances tested.

The tomato plants treated with compounds of the formula I showed consistently less than 20% fungus infestation, compared with that exhibited by control plants (=100% infestation). The compounds Nos. 1, 2, 5, 12, 19, 24, 28, 30, 33, 51, 61, 70, 78, 79, 80, 82, 88, 89, 90, 95, 98, 104, 106, 111 and others prevented fungus infestation completely or almost completely (0–5% infestation).

EXAMPLE 7

Action against Pythium debaryanum on sugar beet (a) Action after soil application The fungus is cultivated on sterile oat seeds and thus added to a soil/sand mixture. The soil infested in this way is filled into flower pots and sown with sugar-beet seeds. Immediately after sowing, the test preparations formulated as wettable powder are poured as aqueous suspensions over the soil (20 ppm of active substance relative to the volume of soil). The pots are then placed in a greenhouse at 20°–24° for 2-3 weeks. The soil during this time is kept uniformly moist by a light spraying with water. In the assessment of the tests, the sprouting of the sugar-beet plants and also the proportion of healthy plants and of diseased plants is determined.

After the treatment with the active substances of the formula I, more than 80% of the sugar-beet plants were sprouting and had a healthy appearance. This result was obtained also with an active-substance concentration in the soil of 6 ppm with use of the compounds Nos. 1, 2, 4, 5, 9, 12, 13, 15, 16, 19, 30, 33, 37, 59, 61, 79, 95, 104, 111 and others.

(b) Action after application as dressing

The fungus is cultivated on sterile oat seeds and thus added to a soil/sand mixture. The soil infested in this manner is filled into flower pots, and sown with sugar-beet seeds which have been dressed with the test preparations formulated as dressing powder (1000 ppm of active substance relative to the weight of seed.) The sown pots are placed in a greenhouse at 20°–24° for 2-3 weeks. The soil during this time is kept uniformly moist by a light spraying with water. In the assessment of the tests, the sprouting of the sugar-beet plants and also the proportion of healthy plants and of diseased plants is determined.

After the treatment with active substances of the formula I, more than 80% of the sugar-beet plants were sprouting and had a healthy appearance.

We claim:

1. A compound of the formula I

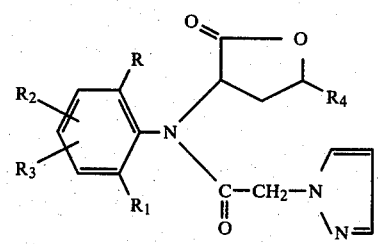

wherein

R represents $C_1$–$C_4$-alkyl, $C_1$–$C_4$-alkoxy or halogen, $R_1$ represents $C_1$–$C_3$-alkyl, $C_1$–$C_4$-alkoxy or halogen, $R_2$ represents hydrogen, $C_1$–$C_3$-alkyl, $C_1$–$C_4$-alkoxy or halogen, $R_3$ represents hydrogen or methyl, with the total number of C atoms of the substituents R, $R_1$, $R_2$ and $R_3$ in the phenyl ring not exceeding the number 8, and $R_4$ represents hydrogen or methyl, 2. A compound according to claim 1 wherein R represents methyl, $R_1$ represents methyl, ethyl, chlorine or bromine, $R_2$ represents hydrogen, halogen or methyl, $R_3$ represents hydrogen or methyl, and $R_4$ represents hydrogen or methyl.

3. A method for combating phytopathogenic fungi which comprises applying to the locus thereof a fungicidally effective amount of a compound according to claim 1 or 2.

4. A fungicidal composition containing as active substance a fungicidally effective amount of a compound according to claim 1 or 2, together with a suitable inert carrier therefor.

* * * * *

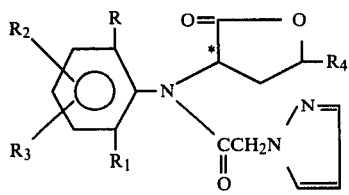

| Compound | R | $R_1$ ($R_1$ = 6-position) | $R_2$ | $R_3$ | $R_4$ |
|---|---|---|---|---|---|
| 104 | $CH_3$ | $CH_3$ | H | H | H |
| 105 | $CH_3$ | $C_2H_5$ | H | H | H |
| 106 | $CH_3$ | $CH_3$ | 3-$CH_3$ | 5-$CH_3$ | H |
| 107 | $CH_3$ | $C_2H_5$ | H | H | $CH_3$ |
| 108 | $CH_3$ | $CH_3$ | H | H | $CH_3$ |
| 109 | $CH_3$ | $CH_3$ | 3-$CH_3$ | 5-$CH_3$ | $CH_3$ |
| 110 | $CH_3$ | $CH_3$ | 3-Cl | H | H |
| 111 | $CH_3$ | $CH_3$ | 3-$CH_3$ | H | H |
| 112 | $CH_3$ | $CH_3$ | 3-$CH_3$ | H | $CH_3$ |
| 113 | $CH_3$ | $CH_3$ | 4-Cl | H | H |
| 114 | $CH_3O$ | $CH_3$ | H | H | H |

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

For application, the compounds of the formula I can be in the following forms (the weight-percentage figures in brackets signify advantageous amounts of active substance):

solid preparations:
dusts and scattering agents (up to 10%), granulates [coated granules, impregnated granules and homogeneous granules] (1 to 80%);

liquid preparations:
(a) water-dispersible concentrates of active substance:
wettable powders and pastes (25 to 90% in the commercial packing, 0.01 to 15% in ready-for-use solutions);
emulsion concentrates and solution concentrates 10 to 50%, 0.01 to 15% in ready-for-use solutions);
(b) solutions (0.1 to 20%).

The active substances of the formula I of the present invention can be formulated for example as follows.

Dust:
The following substances are used to produce a) a 5% dust and b) a 2% dust:
(a). 5 parts of active substance,
95 parts of talcum;
(b) 2 parts of active substance,
1 part of highly dispersed silicic acid, and
97 parts of talcum.

The active substances are mixed and ground with the carriers, and in this form they can be applied by dusting.

Granulate:
The following substances are used to produce a 5% granulate:
5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone; the polyethylene glycol and cetyl polyglycol ether are then added. The solution thus obtained is sprayed onto kaolin, and the acetone is subsequently evaporated off in vacuo. A microgranulate of this kind is particularly suitable for soil application.

Wettable powder:
The following constituents are used to produce (a) a 70% wettable powder, (b) a 40% wettable powder, (c) and (d) a 25% wettable powder, and (e) a 10% wettable powder:
(a) 70 parts of active substance,
5 parts of sodium dibutylnaphthylsulphonate,
3 parts of naphthalenesulphonic acid/phenolsulphonic acid/formaldehyde condensate 3:2:1,
10 parts of kaolin, and
12 parts of Champagne chalk;
(b) 40 parts of active substance,
5 parts of sodium lignin sulphonate,
1 part of sodium dibutylnaphthalenesulphonate, and
54 parts of silicic acid;
(c) 25 parts of active substance,
4.5 parts of calcium lignin sulphonate,
1.9 parts of Champagne chalk/hydroxyethylcellulose mixture (1:1),
1.5 parts of sodium dibutylnaphthalenesulphonate,
19.5 parts of silicic acid,
19.5 parts of Champagne chalk, and
28.1 parts of kaolin;
(d) 25 parts of active substance,
2.5 parts of isooctylphenoxy-polyoxyethyleneethanol,
1.7 parts of Champagne chalk/hydroxyethylcellulose mixture (1:1),
8.3 parts of sodium aluminium silicate,
16.5 parts of kieselguhr, and
46 parts of kaolin; and
(e) 10 parts of active substance,
3 parts of a mixture of the sodium salts of saturated fatty alcohol sulphates,
5 parts of naphthalenesulphonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, which can be diluted with water to give suspensions of the desired concentration, and which can be used in particular for leaf application.

Emulsifiable concentrate:
The following substances are used to produce a 25% emulsifiable concentrate:
25 parts of active substance,
2.5 parts of epoxidised vegetable oil,
10 parts of an alkylarylsulphonate/fatty alcohol polyglycol ether mixture,
5 parts of dimethylformamide, and
57.5 parts of xylene.

Emulsions of the desired concentration can be prepared from these concentrates by dilution with water; and these emulsions are particularly suitable for leaf application.

In order to adapt them to suit prevailing circumstances, the compounds of the formula I can be used, for widening their sphere of action, together with other